United States Patent
Zhao et al.

(10) Patent No.: US 9,194,796 B2
(45) Date of Patent: Nov. 24, 2015

(54) CONCEALED DANGEROUS ARTICLES DETECTION METHOD AND DEVICE

(75) Inventors: Ziran Zhao, Beijing (CN); Yingxin Wang, Beijing (CN); Zhiqiang Chen, Beijing (CN); Wanlong Wu, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 30 days.

(21) Appl. No.: 14/008,903

(22) PCT Filed: Apr. 13, 2012

(86) PCT No.: PCT/CN2012/000513
§ 371 (c)(1),
(2), (4) Date: Oct. 30, 2013

(87) PCT Pub. No.: WO2012/146054
PCT Pub. Date: Nov. 1, 2012

(65) Prior Publication Data
US 2014/0231649 A1 Aug. 21, 2014

(30) Foreign Application Priority Data
Apr. 29, 2011 (CN) .......................... 2011 1 0110590

(51) Int. Cl.
*G01N 21/3581* (2014.01)
*G01V 8/00* (2006.01)
(Continued)

(52) U.S. Cl.
CPC ........... *G01N 21/3581* (2013.01); *G01J 3/0237* (2013.01); *G01V 8/005* (2013.01); *G01N 21/3563* (2013.01)

(58) Field of Classification Search
CPC .... G01N 21/3581; G01V 8/005; G01J 3/0237
See application file for complete search history.

(56) References Cited

U.S. PATENT DOCUMENTS

2002/0067480 A1* 6/2002 Takahashi ...................... 356/317
2004/0140924 A1* 7/2004 Keller et al. .................... 342/22
(Continued)

FOREIGN PATENT DOCUMENTS

CN 1940542 A 4/2007
CN 101251492 A 8/2008
(Continued)

OTHER PUBLICATIONS

Dai, Jianming et al., "Terahertz Wave Generation From Gas Plasma Using a Phase Compensator with Attosecond Phase-Control Accuracy," Applied Physics Letters, vol. 94, Jan. 15, 2009, pp. 021117-2-021117-3.
(Continued)

*Primary Examiner* — David Porta
*Assistant Examiner* — Mindy Vu
(74) *Attorney, Agent, or Firm* — Withrow & Terranova, P.L.L.C.

(57) ABSTRACT

A method and an apparatus for detecting hidden hazardous substance including the steps of: performing terahertz imaging for a detected object; judging whether there is a suspicious area containing the hidden hazardous substance in a terahertz image of the detected object obtained by the terahertz imaging; performing a multi-wavelength spectroscopy measurement to the suspicious area, determining whether the hazardous substance is contained in the suspicious area according to results of multi-wavelength spectroscopy measurement; and outputting the image of the detected object and hazardous substance detecting result. Also disclosed is an apparatus for implementing the method for detecting the hidden hazardous substance according to the present invention. Determination of the hidden hazardous substance can be performed from the perspectives of shape features and substance composition, thus the accuracy of detection is greatly increased.

15 Claims, 3 Drawing Sheets

(51) Int. Cl.
*G01J 3/02* (2006.01)
*G01N 21/3563* (2014.01)

(56) References Cited

U.S. PATENT DOCUMENTS

| | | | |
|---|---|---|---|
| 2006/0022140 A1* | 2/2006 | Connelly et al. | 250/338.1 |
| 2006/0054824 A1* | 3/2006 | Federici et al. | 250/339.02 |
| 2006/0056586 A1 | 3/2006 | Uetake et al. | |
| 2007/0085009 A1 | 4/2007 | Adamski | |
| 2007/0235658 A1* | 10/2007 | Zimdars et al. | 250/390.07 |
| 2009/0180122 A1 | 7/2009 | Frederici | |

FOREIGN PATENT DOCUMENTS

| | | |
|---|---|---|
| CN | 202196176 U | 4/2012 |
| WO | 03102518 A2 | 12/2003 |

OTHER PUBLICATIONS

Hübers, H-W. et al., "Terahertz Imaging System for Stand-Off Detection of Threats," Proceedings of SPIE, vol. 6549, 2007, 7 pages.

Jacobs, E.L. et al., "Concealed Weapon Identification Using Terahertz Imaging Sensors," Proceedings of SPIR, vol. 6212, 10 pages.

Tang, Qingjing and Shao, Jie, "A Study and Application of Long-Distance Explosive Detection Technologies," China Security & Protection, 2009, 9; pp. 40-45.

Zhong, Hua et al., "THz Wave Standoff Detection of Explosive Materials," Proceedings of SPIE, vol. 6212, 8 pages.

International Search Report for PCT/CN2012/000513, mailed Jul. 12, 2012, 8 pages.

Li, Haito et al., "Experimental Studies on Terahertz Continuous Wave Related to Security Inspection," Laser and Infrared, Sep. 2007, vol. 37, No. 9, pp. 876-878.

* cited by examiner

CONCEALED DANGEROUS ARTICLES DETECTION METHOD AND DEVICE

This application is a 35 USC 371 national phase filing of International Application No. PCT/CN2012/000513 filed Apr. 13, 2012, which claims priority to Chinese national application 201110110590.X filed Apr. 29, 2011, the disclosures of which are incorporated herein by reference in their entireties.

FIELD OF THE INVENTION

The present invention falls into the technical field of terahertz sensing. In particular, the present invention relates to a method and apparatus for long-distance locating and identifying hidden hazardous substance by means of active continuous wave terahertz imaging and multi-wavelength spectroscopy.

BACKGROUND ART

Explosives Detection attracts much attention in the field of social and public security. It is of special significance to explore quick and effective detection technologies to safeguard people's life and property security and construct harmonious society. As anti-terrorism intensity increases and as security check and anti-explosive measures are reinforced, the existing short-distance explosive detecting and identifying apparatuses are playing a substantial role. However, criminals continually enhance their counter-reconnaissance awareness and the explosive apparatus varies therewith, hazardous substance may explode during the inspection stage, thus threaten security of inspectors and detecting apparatuses, so it is the most optimal means to perform a long-distance detection.

Currently, the technologies meeting the demand for long-distance explosive detection to a certain extent mainly includes X-ray backscattering imaging, laser spectroscopy, thermal imaging, millimeter wave and terahertz technologies and the like (1. A study and Application of Long-distance Explosive Detection Technologies, Qianjing TANG and Jie SHAO, China Security & Protection, 2009, 9:40-45, which is incorporated herein by reference in its entirety). The X-ray backscattering imaging technology uses the back-scattered X-rays for imaging the detected object, wherein the X-ray energy used therefor is lower than the energy used for transmission imaging, and the potential detection distance for the X-ray backscattering imaging technology is 15 meters, which is sufficient for distinguishing the explosives from the background. Since the X-rays have ionization-inducing property, they do harm to people's health to a certain degree. Laser spectroscopy judges whether there is an explosive mainly by taking advantage of the laser with a particular wavelength absorbed or emitted by the object being detected upon laser radiation, for example, Raman spectrum, laser induced fluorescence spectrum and photoacoustic spectrum. The laser spectroscopy technology is advantageous in that laser has a good propagation characteristic and meets the demand for long-distance detection, and this technology is disadvantageous in that laser cannot penetrate an opaque object and therefore cannot be used to detect hidden explosives. Thermal imaging technology performs detection mainly by means of the temperature difference between the hidden substance and the surface. This technology is remarkably advantageous for detecting body bombs, but flow of air and other thermal sources may have an influence on the detecting results. Meanwhile, this technology can only provide information about the shape of the hidden substance so that explosives cannot be discriminated from the perspective of the substance composition, therefore the detection capability of this kind of technology is limited. As to millimeter wave technology, images are formed by electromagnetic radiation of millimeter wave band emitted by the detected object itself or reflected back from the object. The millimeter wave has excellent penetrability through atmosphere and clothing and is capable of detecting hidden weapons at a long distance, but does not have an ability to identify substance composition. Terahertz radiation generally refers to electromagnetic waves with a frequency in a range of 0.1-10 THz and it has unique properties in the following aspects: first, a lot of organic molecules are characterized by characteristic absorption and dispersion within a terahertz frequency band so that the terahertz spectrum of a substance exhibits a "fingerprint" property. Hence, a substance species and composition can be identified by means of terahertz spectroscopy technology; secondly, terahertz radiation has a very strong penetration through many non-metallic and non-polarity substances and can directly detect hidden hazardous substance; besides, terahertz electromagnetic waves do not have ionization-inducing property as the X-rays and is not harmful to the materials and human body, so terahertz technology embraces an excellent application prospect in respect of explosive detection.

In 2006, US landforce RDECOM CERDEC Night Vision and Electronic Sensor Laboratory developed a set of 640 GHz active imaging instrument which can detect concealed weapons (2. E. L. Jacobs, S. Moyer, C. C. Franck, et al., Concealed Weapon Identification Using Terahertz Imaging Sensors. Proc. Of SPIE, 2006, 6212: 62120J, which is incorporated herein by reference in its entirety). Its detection distance is about 1.5m, the confocal imaging manner employed ensures high resolution and signal-to-noise ratio (SNR), but the scanning speed thereof is slow. At the same time, German Aerospace Research Center conducted a research of stand-off terahertz imaging for metal hazardous substances concealed below peoples' clothes for the anti-terrorism purpose, and in 2007 successfully developed an imaging system prototype machine with an operation frequency of 0.8 THz, a detection distance up to 20 m and a resolution of less than 2 cm (3. H.-W. Hübers, A. D. Semonov, H. Richter, et al., Terahertz imaging system for stand-off detection of threats, Proc. Of SPIE, 2007, 6549:65490A, which is incorporated herein by reference in its entirety), which can reach a scanning speed approaching real-time image collection. The above research indicates that it is feasible to take advantage of active terahertz radiation for imaging and positioning a suspicious object at a long distance, but it needs to combine with spectrum information to identify with respect to the explosive detection. Furthermore, such research is still in a bench test stage and not put into practical application yet, which need to be further developed.

Few studies at home and abroad are carried out for long-distance terahertz spectroscopy and they are all in an exploration stage. In 2006, US RPI Terahertz Research Center adopted conventional terahertz time-domain spectroscopy technology to detect an explosive sample at a distal distance, observed RDX 0.82 THz absorption peak even at a propagation distance of 30 m and preliminarily found that long-distance explosive identification is feasible (4. H. Zhong, A. Redo, Y. Chen, et al., THz wave standoff detection of explosive materials, Proc. of SPIE, 2006, 6212: 62120L, which is incorporated herein by reference in its entirety). However, atmospheric absorption results in serious distortion of spectrum, undesirable signal-to-noise ratio and is inapplicable for practical application. This research center further proposed a new technology of generating pulsed terahertz radiation by inducing air plasma by means of femtosecond laser (5. J. Dai and X.-C. Zhang, Terahertz wave generation from gas plasma using a phase compensator with attosecond phase-control accuracy. Appl. Phys. Lett., 2009, 94: 021117, which is incorporated herein by reference in its entirety). As such, visible light in the atmosphere with good transmission property may be emitted to nearby the detected object at a distal distance to produce terahertz radiation so as to avoid attenuation caused by the atmosphere to the terahertz radiation, then the explosive is identified by spectroscopy. However, long-distance detection of a reflected signal is confronted with difficulty, pure spectroscopy technology only detects one measuring point of the object and does not have a spatial orientation capability. Therefore, this technology needs to combine with an imaging technology to meet demands of practical application.

SUMMARY OF THE INVENTION

In order to overcome the drawbacks in the above prior arts, the present invention provides a new long-distance hidden hazardous substance detecting method. The key of the method lies in that, based on the high power and frequency tuning properties of the continuous wave terahertz radiation, first quick locating the suspicious object on basis of the shape information reflected by terahertz imaging, then selecting certain frequency bands with good atmospheric transmittance to perform terahertz spectrum discrimination measurement to further identify whether there is hazardous substance.

The term "long-distance" used in the present application is generally defined as a range of 5 m-20 m away from a detected object. However, the apparatus and method of the present invention are also applicable to the detection of hidden hazardous substance at a shorter distance or at a longer distance.

The technical solution of the present invention is implemented in the following manners:

A method for detecting hidden hazardous substance, comprising the following steps: performing terahertz imaging for a detected object; judging whether there is a suspicious area containing the hidden hazardous substance in a terahertz image of the detected object obtained by terahertz imaging; performing a multi-wavelength spectroscopy measurement to the suspicious area that might contain the hazardous substance, and determining whether the hazardous substance is contained in the suspicious area according to results of multi-wavelength spectroscopy measurement; and outputting the terahertz image of the detected object and the hazardous substance detecting result.

According to one aspect of the method of the present invention, the step of performing terahertz imaging for the detected object may comprise: adjusting a terahertz emitter to operate at an imaging wavelength; collimating and focusing the terahertz radiation outputted by the terahertz emitter, and transmitting the terahertz radiation to the detected object; collecting the terahertz radiation reflected back by the detected object through a terahertz detector to obtain the information of one pixel point of the detected object; and enabling a terahertz wave beam to scan each pixel in a field of vision through a wave beam scanning control system so as to acquire a terahertz reflection image of the detected object.

According to another aspect of the method of the present invention, the step of judging whether there is a suspicious area containing the hidden hazardous substance in a terahertz image of the detected object obtained by terahertz imaging may comprise: judging whether there is a suspicious area containing hazardous substance in the scanning image through a data acquisition and processing system based on the shape characteristics and gray-scale value characteristics obtained by the terahertz reflection image, meanwhile, exactly locating the suspicious area.

According to a further aspect of the method of the present invention, the step of performing a multi-wavelength spectroscopy measurement to the suspicious area that might contain the hazardous substance may further comprise: selecting a certain point of interest in the suspicious area, performing the multi-wavelength spectroscopy measurement for the point of interest, establishing a terahertz multi-wavelength reflection spectrum identification model, and using a pattern recognition method to identify whether there is hazardous substance in the suspicious area.

According to a further aspect of the method of the present invention, the step of adjusting a terahertz emitter to operate at an imaging wavelength may further comprise: a) selecting a frequency window with good transmittance according to the transmission properties of the terahertz radiation in the atmosphere, and determining the operating wavelength range of a terahertz radiation source; b) comprehensively analyzing a transmitting power of the terahertz radiation source and an influence of the wavelength on an imaging signal-to-noise ratio and a spatial resolution, and meanwhile taking into account the range of wavelength defined in step a) to determine an optimal imaging wavelength.

According to another aspect of the method of the present invention, the wave beam scanning control system may comprise a terahertz wave beam scanning device and a terahertz wave beam scanning control unit. The step of enabling a terahertz wave beam to scan each pixel in a field of vision through the wave beam scanning control system may further comprise: enabling the terahertz wave beam scanning control unit to send a signal to the terahertz wave beam scanning device, and adjusting a wave beam scanning module in the terahertz wave beam scanning device to change the light spot position of the terahertz wave beam on the detected object.

According to a further aspect of the method of the present invention, the wave beam scanning module may be a galvanometer mirror.

According to a further aspect of the method of the present invention, the wave beam scanning control system may comprise a terahertz wave beam scanning device and a terahertz wave beam scanning control unit. The step of enabling a terahertz wave beam to scan each pixel in a field of vision through the wave beam scanning control system may further comprise: the terahertz wave beam scanning device bears a system comprised of the terahertz emitter, the terahertz detector and the terahertz optical assembly to implement a translational movement, enabling the terahertz wave beam scanning control unit to send a signal to the terahertz wave beam scanning device, and adjusting the spatial position of the assembly to change the light spot position of the incident terahertz wave beam on the detected object.

According to a further aspect of the method of the present invention, the step of performing a multi-wavelength spectroscopy measurement to the suspicious area that might contain the hazardous substance may further comprise: selectively adjusting the radiation wavelength of the terahertz emitter through the wavelength tuning control unit to enable the terahertz emitter to operate at a wavelength required by the multi-wavelength spectroscopy.

An apparatus for detecting hidden hazardous substance, comprising: a terahertz emitting device configured to produce wavelength tunable continuous wave terahertz radiation for irradiating the detected object and interacting with the object; a terahertz detector configured to receive terahertz radiation reflected back from the detected object; a terahertz optical assembly configured to collimate the wave beam produced by the terahertz emitting device, and focus it to the detected object, and meanwhile collect the terahertz wave beam reflected back from the detected object to the terahertz detector; a wave beam scanning control system configured to adjust the spatial position of the terahertz wave beam incident to the detected object; and a data acquisition and processing system connected to the terahertz emitting device, the terahertz detector and the wave beam scanning control system and configured to control the coordination of the terahertz emitting device, the terahertz detector and the wave beam scanning control system in the apparatus, build a terahertz reflection image of the detected object, judge whether there is a suspicious area containing hazardous substance in the terahertz reflection image based on shape characteristics and gray-scale value characteristics obtained by the terahertz reflection image, searching and locating the suspicious area, then perform analysis and processing for the multi-wavelength reflection spectrum data of measurement points of interest in the suspicious area, and present hazardous substance identifying result.

According to one aspect of an apparatus of the present invention, the terahertz emitting device may further comprise a terahertz emitter and a wavelength tuning control unit, wherein the wavelength tuning control unit is connected to the terahertz emitter, to selectively adjust the radiation wavelength of the terahertz emitter.

According to another aspect of the apparatus of the present invention, the terahertz emitter may be a Gunn oscillator and a frequency multiplier, a backward wave tube, a parameter oscillator, or a quantum cascade laser.

According to another aspect of the apparatus of the present invention, the terahertz detector may be a Schottky diode, a superconducting-insulator-superconducting junction frequency mixer, or a bolometer.

According to another aspect of the apparatus of the present invention, the wave beam scanning control system comprises a terahertz wave beam scanning device and a terahertz wave beam scanning control unit. The terahertz wave beam scanning control unit is connected to the terahertz wave beam scanning device. The terahertz wave beam scanning device comprises a wave beam scanning module and is used to adjust and monitor the wave beam scanning module in real time to complete setting and reading of the wave beam spatial position information.

According to a further aspect of the apparatus of the present invention, the wave beam scanning module may be a galvanometer mirror.

According to a further aspect of the apparatus of the present invention, the terahertz wave beam scanning device may be a mechanical translational table which carries a system comprising the terahertz emitting device, the terahertz detector and the terahertz optical assembly and performs 2-dimensional point-by-point scanning of the detected object to obtain an image of the detected object.

According to a further aspect of the apparatus of the present invention, the terahertz optical assembly may comprise a beam splitter which is responsible for collimating the wave beam produced by the terahertz emitting device and collecting the terahertz wave beam reflected back from the detected object to the terahertz detector, a planar mirror and a parabolic mirror or an elliptical mirror or lens for focusing the terahertz wave beam on the detected object.

By using the above method and structure, the present invention has the following advantages as compared with the prior art:

1) The method of combining continuous wave terahertz imaging and continuous wave multi-wavelength spectroscopy as proposed by the present invention can achieve identification of the hidden hazardous substance simultaneously from perspectives of both shape characteristics and substance compositions;
2) The apparatus provided by the present invention quickly locates the suspicious area in which hazardous substance might be hidden through terahertz imaging, then only selects a certain point of interest in the area to perform further spectroscopy and identification, without the need of conducting spectroscopic imaging for the whole scanned area. Therefore, the apparatus has a fast measurement speed and can substantially improve the detecting efficiency;
3) The continuous wave multi-wavelength spectroscopy method adopted by the present invention can avoid the influence produced by atmospheric absorption, and ensure the feasibility of long-distance detection. Furthermore, the apparatus proposed by the present invention uses a wavelength tunable continuous wave terahertz radiation source, which has a higher average output power than that of a commonly-used pulsed source. Therefore, the apparatus exhibits better penetrability through barrier materials, a higher signal-and-noise ratio and better applicability.

BRIEF DESCRIPTION OF THE DRAWINGS

The above features and advantages of the present invention will be made more apparent by the following detailed description with reference to the figures, wherein.

DETAILED DESCRIPTION OF THE PREFERRED EMBODIMENTS

Preferred embodiments of the present invention will be described hereunder in detail with reference to the accompanied drawings.

Figure 1:
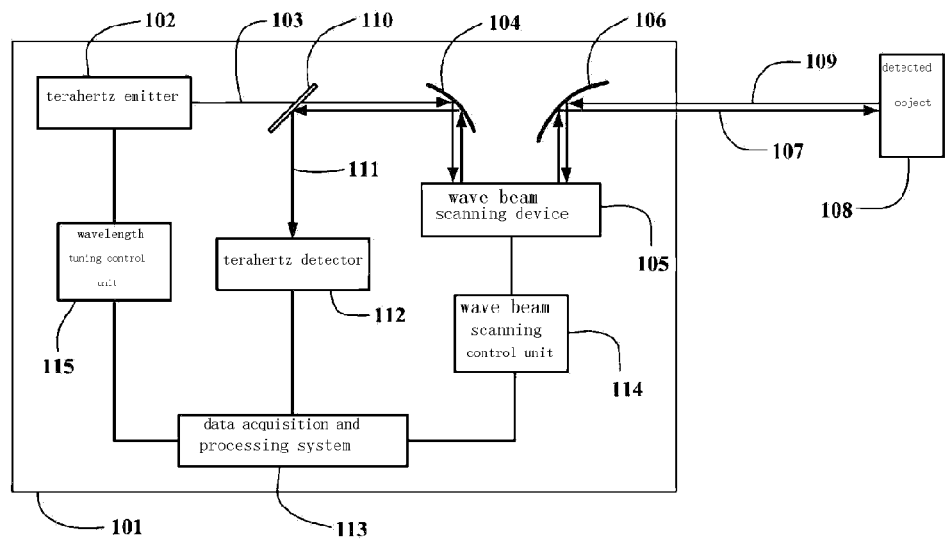
FIG. 1 is a schematic view showing the structure of the first embodiment of an apparatus for performing long-distance detection of an explosive by using terahertz imaging and multi-wavelength spectroscopy.

FIG. 1 is a schematic view showing the structure of the first embodiment of an apparatus of performing long-distance detection of an explosive by using terahertz imaging and multi-wavelength spectroscopy. As shown in FIG. 1, the apparatus 101 according to the first embodiment of the present invention comprises a terahertz emitter 102 and its wavelength tuning control unit 115, a terahertz detector 112;

a wave beam scanning device 105 and its wave beam scanning control unit 114; a terahertz collimating element 104, a focusing element 106, a beam splitter 110; and a computer-based data acquisition and processing system 113. The terahertz emitters 102 and its wavelength tuning control unit 115 constitute a terahertz emitting device configured to produce wavelength tunable continuous wave terahertz radiation for irradiating the detected object and interacting with the detected object. The wave beam scanning device 105 and its wave beam scanning control unit 114 constitute a wave beam scanning controlling system. The terahertz collimating element 104, the focusing element 106 and the beam splitter 110 constitute a terahertz optical assembly for transmitting radiated wave beams.

The terahertz emitter 102 produces continuous wave terahertz radiation 103 with a wavelength of $\lambda_0$ (the corresponding frequency is $f_0$), which, after passing the beam splitter 110 and the terahertz collimating element 104 (which may be parabolic mirror or lens), reaches the wave beam scanning device 105, and which subsequent propagation direction is controlled by the wave beam scanning device 105; the focusing element 106 (which may be parabolic mirror or lens) converges an incident terahertz wave beam 107 at a distal specific measuring point on a detected object 108; a wave beam 109 reflected by the object 108 returns along a propagation path of the incident wave beam, and then is reflected by the beam splitter 110, an intensity of a wave beam 111 reflected by the beam splitter is measured by the terahertz detector 112; the data acquisition and processing system 113 reads the intensity of the terahertz reflected wave at the specific measuring point. The wave beam scanning control unit 114 sends a signal to the wave beam scanning device 105, the wave beam scanning device 105 is adjusted by means of mechanical members therein to change a light spot position of the incident wave beam 107 on the detected object 108; the data acquisition and processing system 113 coordinates with the wave beam scanning control unit 114 and the terahertz detector 112 to obtain terahertz reflected wave intensity at different positions in an area of the detected object 108 to be scanned and finally form a terahertz reflection image of the detected object 108. The wavelength tuning control unit 115 tunes an operation wavelength of the terahertz emitter 102, and sets the imaging wavelength $\lambda_0$ and the spectroscopy wavelength $\{\lambda_1, \lambda_2, \ldots, \lambda_n\}$.

Figure 2:
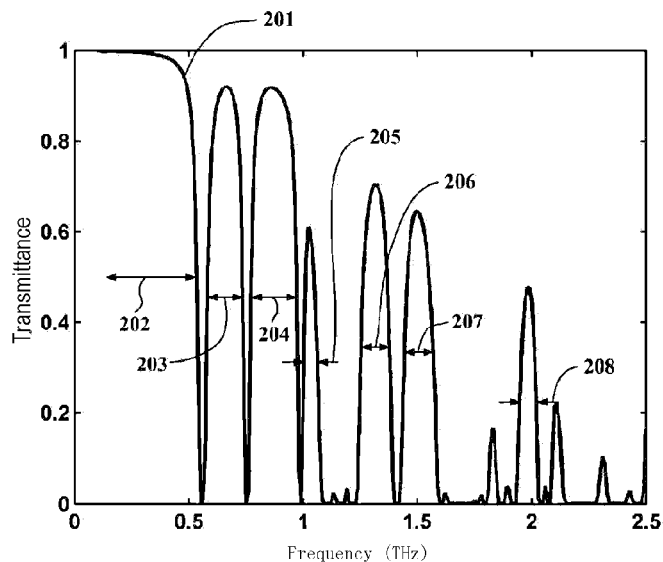
FIG. 2 illustrates an atmosphere transmission spectrum of terahertz radiation (at a standard atmospheric pressure, a temperature of 20° C., a relative humidity of 40%, and a transmission distance of 20 m)

FIG. 2 illustrates an atmosphere transmission spectrum of terahertz radiation in a range of 0.1-2.5 THz obtained by calculating from HITRAN molecule absorption spectrum database, under the following conditions: a standard atmospheric pressure, a temperature of 20° C., a steam relative humidity of 40%, and an assumed transmission distance of terahertz radiation of 20 m. As shown in FIG. 2, the attenuation rules reflected by the transmission spectrum curve 201 indicate that transmission of the terahertz radiation in the atmosphere has a series of frequency windows with a higher transmittance, for example, the frequency intervals 202-208 marked in the figure. These data serve as a basis for the wavelength tuning control unit 115 to set an operation wavelength of the terahertz emitter 102. In an imaging mode, the system operates at a single wavelength $\lambda_0$, and may select a wavelength value corresponding to any frequency in the intervals 202-208. Certainly, a tunable range of the wavelength outputted by the terahertz emitter needs to be taken into consideration simultaneously. In the multi-wavelength spectroscopy mode, the system operates at a series wavelengths $\{\lambda_1, \lambda_2, \ldots, \lambda_n\}$ which can be respectively selected from the intervals 202-208, and meanwhile thoughts are given to whether they correspond to spectrum features of the explosive, for example, the RDX explosive has an absorption value nearby 0.8 THz and this frequency is located at the interval 204 (with a transmittance greater than 80%).

Figure 3:
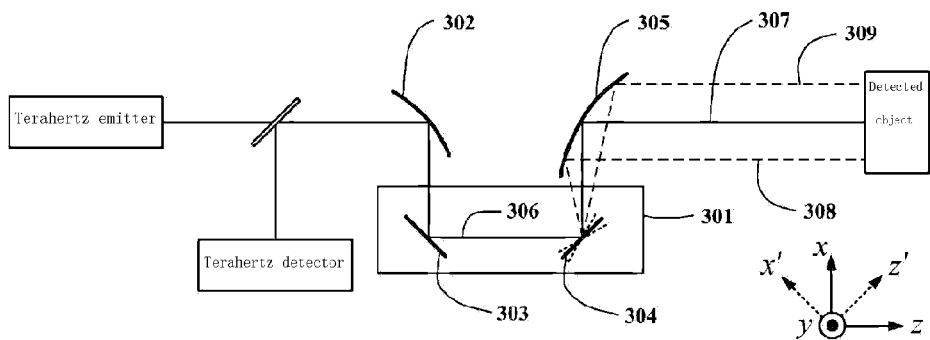
FIG. 3 is a schematic view of terahertz wave beam scanning.

FIG. 3 is a schematic view of terahertz wave beam scanning. A wave beam scanning module 301 may comprise two uni-axial galvanometer mirror or one dual-axis galvanometer mirror. As shown in FIG. 3, the wave beam emitted by the terahertz emitter is reflected and collimated by a parabolic mirror 302, reflected by galvanometer mirrors 303, 304 in the wave beam scanning module 301 and then is incident to a parabolic mirror 305, and then is focused on the detected object. The galvanometer mirrors 303, 304 may be in the form of planar mirrors and act under the interaction of mechanical members in the wave beam scanning device. The galvanometer mirror 303 rotates about an axis x' so that the wave beam 306 moves in a y-z plane, and a light spot position of the incident wave beam on the object moves therewith and achieves transverse (line-by-line) scanning of the wave beam; the galvanometer mirror 304 is located a focal point of the parabolic mirror 305 and rotates about y axis so that the wave beam 307 moves in a x-z plane and achieves longitudinal (column-by-column) scanning of the wave beam. Wave beams 308 and 309 correspond to the scanning of the galvanometer mirror 304 at two different rotation angles. By means of control of the coordination of the galvanometer mirrors 303 and 304, point-by-point quick scanning of the terahertz wave beam is achieved, reflected light intensity of each pixel in a 2-dimensional area of the detected object is finally obtained.

Figure 4:
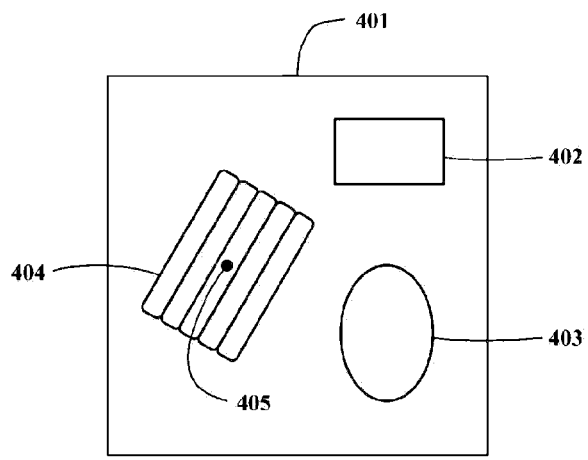
FIG. 4 is a schematic view of locating and identifying a suspicious area in a terahertz image.

FIG. 4 is a schematic view of locating and identifying a suspicious area in a terahertz image. As shown in FIG. 4, a reflection image 401 is obtained after the apparatus 101 according to an embodiment of the present invention performs scanning and imaging for the detected object, wherein three different areas 402, 303, 404 are included. The image is further processed by a computer, the areas are analyzed according to the shape characteristics and gray value characteristics, the suspicious area 404 is automatically searched out, i.e., the area might include a concealed explosive, then a certain point 405 in the area is selected for subsequent measurement. Spatial coordinates corresponding to the measuring point are extracted, the wave beam scanning device is adjusted to orientate the wave beam light spot incident on the object on the point, and then the multi-wavelength spectroscopy measurement is performed.

Figure 5:
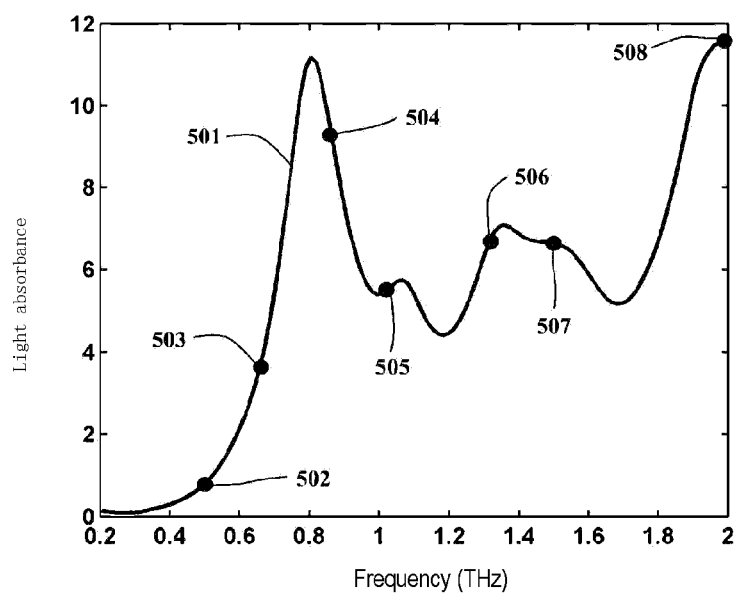
FIG. 5 illustrates terahertz absorption spectrum of the explosive RDX and sampling points selected for multi-wavelength spectroscopy.

The output wavelengths $\{\lambda_1, \lambda_2, \ldots, \lambda_n\}$ of the terahertz emitter are tuned in the transmission windows shown in FIG. 2, a terahertz reflectivity of a point 405 of interest corresponding to different wavelengths is measured so as to obtain multi-wavelength reflection spectrum data in the suspicious area. FIG. 5 shows a terahertz absorption spectrum 501 of the RDX explosive and seven typical sampling points 502-508 selected for the multi-wavelength spectroscopy, wherein the sampling points 502-508 sequentially correspond to 0.50, 0.66, 0.86, 1.02, 1.32, 1.50 and 1.99 THz, and they (except for the first point) are located at a center of each atmosphere transmission window, and can reflect main spectrum characteristics of the RDX. Assuming that theses frequencies are all falling in a tunable range of the terahertz emitter, reflectivity corresponding to them is measured in turn so as to obtain a 1-dimensional vector $S=\{r_1, r_2, \ldots, r_7\}$ with a length of 7, and the vector is considered as a multi-wavelength reflection spectrum of the suspicious area. A specific method of measuring the reflectivity is placing a reflection mirror at the detected object, recording a reflected light intensity corresponding to a certain wavelength, marking it as a reference signal A, and when a suspicious object is detected, measuring a reflected light intensity at the same wavelength, marking it as an object signal B, whereby the reflectivity of the object at this wavelength is r=B/A. Since the terahertz emitter outputs different power under different wavelengths and the atmosphere attenuates the terahertz radiation to different degrees, the operation of calculating the reflectivity by the reference signal is equivalent to calibrating the influence of the two factors.

Then, whether the suspicious area includes an explosive is identified according to the measured spectrum S. This needs to build a database including various typical explosive spectrums. Hence, first, standard testing samples of various typical explosives are produced, then their multi-wavelength reflection spectrums are measured by following the previous steps and totally stored as a spectrum database. On this basis, a multi-wavelength spectrum identification model is established by using a pattern recognition method such as an artificial neural network or a support vector machine, the class of the actually measured spectrum S is judged by using the model so as to identify whether the area to be analyzed includes an explosive. So far, the long-distance locating and identification of the hidden explosive is accomplished in a manner of combining the continuous wave terahertz imaging and the multi-wavelength spectroscopy.

Figure 6:
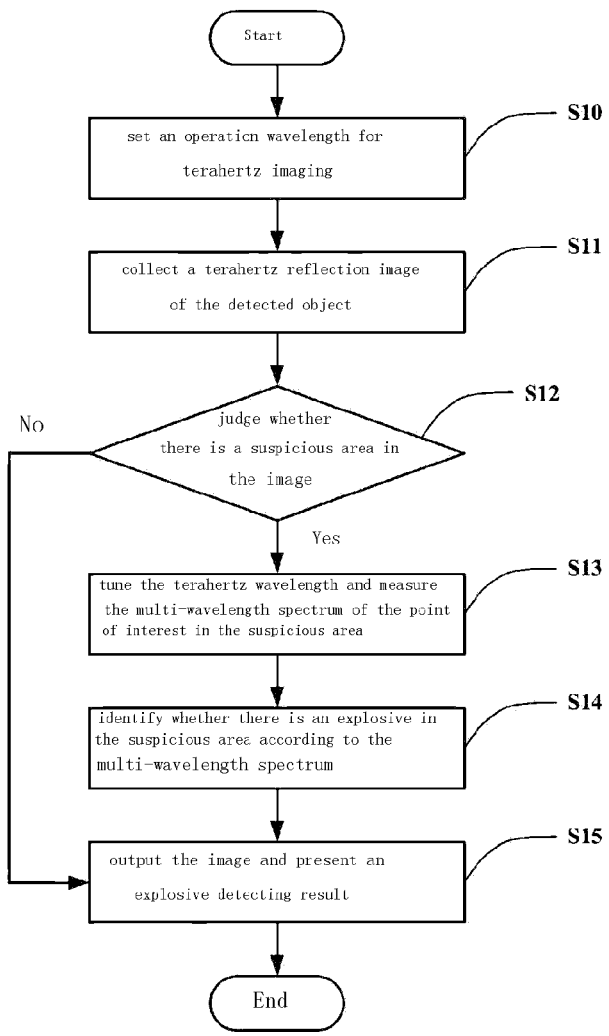
FIG. 6 is a flow chart of a method of detecting a hidden explosive according to the first embodiment of the present invention.

FIG. 6 is a flow chart of a method of detecting a hidden explosive according to the first embodiment of the present invention. As shown in FIG. 6, first, at step S10, a user adjusts an operation wavelength of the terahertz emitter 102 by the wavelength tuning control unit 115 and sets an imaging wavelength $\lambda_0$.

Then, at step S11, the wave beam scanning device 105 is controlled by the wave beam scanning control unit 114, the light spot position of the terahertz incident wave beam 107 on the detected object 108 is adjusted, and meanwhile, the data acquisition and processing system 113 reads the intensity of the terahertz reflected wave at each measuring point to acquire the terahertz reflection image 401 of the detected object 108.

Thereafter, at step S12, each area in the image 401 is analyzed. Since the explosive might be different from a conventional object in their shapes and in their reflecting intensities to the terahertz waves, the difference in image gray-scale values may appear. Whether there exists the suspicious area 404 in which the explosive might be concealed is judged according to the shape characteristics and gray-scale value characteristics obtained by the terahertz reflection images and based on the experience.

If the judging result is that the suspicious area does not exist, then go directly to step S15 to display the image of the detected object to the user and present an explosive detecting result.

If the judging result is that the suspicious area does exist, at step S13 the operation wavelength of the terahertz emitter 102 is further adjusted, the spectroscopy wavelength $\{\lambda_1, \lambda_2, \ldots, \lambda_n\}$ is set, the light intensity at the certain point 405 in the suspicious area 404 is measured at these wavelengths to obtain the multi-wavelength spectrum data. Then, at step S414, the species of substance in the suspicious area is identified according to the measured multi-wavelength spectrum to judge whether the explosive is contained. Finally, at step S15 the obtained terahertz reflection image is displayed on the screen and the explosive detecting result is presented.

Figure 7:
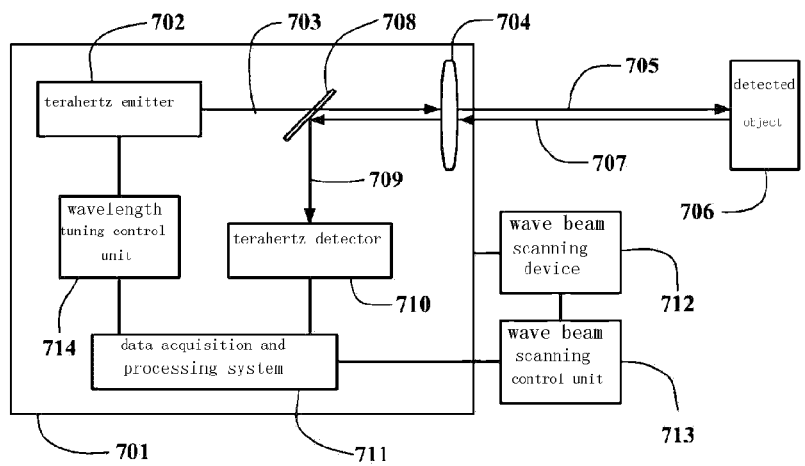
FIG. 7 is a schematic view showing the structure of the second embodiment of an apparatus for performing long-distance detection of an explosive by using terahertz imaging and multi-wavelength spectroscopy.

FIG. 7 is a schematic view showing the structure of a second embodiment of an apparatus of performing long-distance detection of an explosive by using terahertz imaging and multi-wavelength spectroscopy. As shown in FIG. 7, the second embodiment of the present invention comprises a terahertz emitter 702 and its wavelength tuning control unit 714, a terahertz detector 710; a wave beam scanning device 712 and its wave beam scanning control unit 713; a terahertz focusing element 704, a beam splitter 708; and a computer-based data acquisition and processing system 711. The terahertz emitters 702 and its wavelength tuning control unit 714 constitute a terahertz emitting device configured to produce wavelength tunable continuous wave terahertz radiation for irradiating the detected object and interacting with the object. The wave beam scanning device 712 and its wave beam scanning control unit 713 constitute a wave beam scanning control system. The terahertz focusing element 704 and the beam splitter 708 constitute a terahertz optical assembly for transmitting radiated wave beams.

The terahertz emitter 702 produces continuous wave terahertz radiation 703, which, after passing the beam splitter 708, reaches the focusing element 704 (which may be lens or parabolic mirror) to converge a terahertz wave beam 705 at a distal specific measuring point on a detected object 706; a wave beam 707 reflected by the object 706 returns along a propagation path of the incident wave beam, and then is reflected by the beam splitter 708, the intensity of a wave beam 709 reflected by the beam splitter is measured by the detector 710; the data acquisition and processing system 711 reads the intensity of the terahertz reflected wave at the specific measuring point. The wave beam scanning device 712 bears a system 701 comprised of a terahertz source, a detector and an optical assembly to implement a translational movement, the wave beam scanning control unit 713 sends a signal to the wave beam scanning device 712, the spatial position of the system 701 is adjusted to change a light spot position of the incident wave beam 705 on the detected object 706; the data acquisition and processing system 711 coordinates with the wave beam scanning control unit 713 and the terahertz detector 710 to acquire terahertz reflected wave intensity at different positions in an area of the detected object 706 to be scanned and finally build a terahertz reflection image of the detected object 706.

The multi-wavelength spectroscopy procedure and the explosive-detecting flowchart according to the second embodiment of the present invention are substantively identical with the first embodiment and will not be described in detail herein any longer.

The above description is only embodiments for implementing the present invention. Those skilled in the art should understand that any modifications or partial substitution without departing from the scope of the present invention all should fall within the scope defined by the appended claims of the present invention. For example, although the above embodiments of the present invention are concerned with long-distance detecting method and apparatus of an explosive, it should be noted that the present invention is also applicable to long-distance detecting methods and apparatus of inflammable, explosive and highly corrosive hazardous substance. In addition, the present invention is also completely applicable to short-distance detecting methods and apparatus of various hazardous substance containing explosives. Hence, the protection scope of the present invention should be subjected to the scope defined by the appended claim set.

The invention claimed is:

1. A method for detecting hidden hazardous substance, comprising the following steps:
   producing wavelength tunable continuous wave terahertz radiation for irradiating a detected object and interacting with the object by a terahertz emitting device;
   receiving terahertz radiation reflected back from the detected object by a terahertz detector;

collimating a wave beam produced by the terahertz emitting device and focusing the wave beam to the detected object, meanwhile, collecting a terahertz wave beam reflected back from the detected object to the terahertz detector by a terahertz optical assembly;

adjusting a spatial position of the terahertz wave beam incident to the detected object by a wave beam scanning control system; and controlling coordination of the terahertz emitting device, the terahertz detector and the wave beam scanning control system in an apparatus, building a terahertz reflection image of the detected object, judging whether there is a suspicious area containing hazardous substance in the terahertz reflection image based on shape characteristics and gray-scale value characteristics obtained by the terahertz reflection image, searching and locating the suspicious area, performing analysis and processing for multi-wavelength reflection spectrum data of measurement points of interest in the suspicious area, and presenting a hazardous substance identifying result by a data acquisition and processing system.

2. The method according to claim 1, further comprising:

adjusting the terahertz emitting device to operate at an imaging wavelength;

collecting the terahertz radiation reflected back by the detected object through the terahertz detector to obtain information of one pixel point of the detected object; and enabling the terahertz wave beam to scan each pixel in a field of vision through the wave beam scanning control system so as to acquire the terahertz reflection image of the detected object.

3. The method according to claim 2, wherein the step of adjusting the terahertz emitting device to operate at an imaging wavelength further comprises:

a) selecting a frequency window with good transmittance according to transmission properties of the terahertz radiation in the atmosphere, and determining an operating wavelength range of a terahertz radiation source;

b) comprehensively analyzing a transmitting power of the terahertz radiation source and an influence of the wavelength on an imaging signal-to-noise ratio and a spatial resolution, and meanwhile taking into account the range of wavelength defined in step a) to determine an optimal imaging wavelength.

4. The method according to claim 2, wherein the wave beam scanning control system comprises a terahertz wave beam scanning device and a terahertz wave beam scanning control unit, the step of enabling the terahertz wave beam to scan each pixel in the field of vision through the wave beam scanning control system further comprises: enabling the terahertz wave beam scanning control unit to send a signal to the terahertz wave beam scanning device, and adjusting a wave beam scanning module in the terahertz wave beam scanning device to change a light spot position of the terahertz wave beam on the detected object.

5. The method according to claim 4, wherein the wave beam scanning module is a galvanometer mirror.

6. The method according to claim 2, wherein the wave beam scanning control system comprises a terahertz wave beam scanning device and a terahertz wave beam scanning control unit, the step of enabling the terahertz wave beam to scan each pixel in the field of vision through the wave beam scanning control system further comprises: the terahertz wave beam scanning device bearing a system comprised of the terahertz emitting device, the terahertz detector and the terahertz optical assembly to implement a translational movement, enabling the terahertz wave beam scanning control unit to send a signal to the terahertz wave beam scanning device, and adjusting the spatial position of the assembly to change a light spot position of the incident terahertz wave beam on the detected object.

7. The method according to claim 1, further comprising selectively adjusting a radiation wavelength of the terahertz emitting device through a wavelength tuning control unit to enable the terahertz emitting device to operate at a wavelength required by a multi-wavelength spectroscopy.

8. An apparatus for implementing a method for detecting hidden hazardous substance comprising:

a terahertz emitting device configured to produce wavelength tunable continuous wave terahertz radiation for irradiating a detected object and interacting with the object;

a terahertz detector configured to receive terahertz radiation reflected back from the detected object;

a terahertz optical assembly configured to collimate a wave beam produced by the terahertz emitting device, and focus it to the detected object, and meanwhile collect a terahertz wave beam reflected back from the detected object to the terahertz detector;

a wave beam scanning control system configured to adjust a spatial position of the terahertz wave beam incident to the detected object; and a data acquisition and processing system connected to the terahertz emitting device, the terahertz detector and the wave beam scanning control system and configured to control coordination of the terahertz emitting device, the terahertz detector and the wave beam scanning control system in an apparatus, build a terahertz reflection image of the detected object, judge whether there is a suspicious area containing hazardous substance in the terahertz reflection image based on shape characteristics and gray-scale value characteristics obtained by the terahertz reflection image, searching and locating the suspicious area, then perform analysis and processing for multi-wavelength reflection spectrum data of measurement points of interest in the suspicious area, and present a hazardous substance identifying result.

9. The apparatus according to claim 8, wherein the terahertz emitting device comprises a terahertz emitter and a wavelength tuning control unit, wherein the wavelength tuning control unit is connected to the terahertz emitter, to selectively adjust radiation wavelength of the terahertz emitter.

10. The apparatus according to claim 9, wherein the terahertz emitter is a Gunn oscillator and a frequency multiplier, a backward wave tube, a parameter oscillator, or a quantum cascade laser.

11. The apparatus according to claim 9, wherein the terahertz detector is a Schottky diode, a superconducting-insulator-superconducting junction frequency mixer, or a bolometer.

12. The apparatus according to claim 8, wherein the wave beam scanning control system comprises a terahertz wave beam scanning device and a terahertz wave beam scanning control unit, the terahertz wave beam scanning control unit is connected to the terahertz wave beam scanning device, the terahertz wave beam scanning device comprises a wave beam scanning module and is used to adjust and monitor the wave beam scanning module in real time to complete setting and reading of the wave beam spatial position information.

13. The apparatus according to claim 12, wherein the wave beam scanning module is a galvanometer mirror.

14. The apparatus according to claim 12, wherein the terahertz wave beam scanning device is a mechanical translational table which carries a system comprising the terahertz emitting device, the terahertz detector and the terahertz optical assembly and performs 2-dimensional point-by-point scanning of the detected object to obtain an image of the detected object.

15. The apparatus according to claim 8, wherein the terahertz optical assembly comprises a beam splitter which is responsible for collimating the wave beam produced by the terahertz emitting device and collecting the terahertz wave beam reflected back from the detected object to the terahertz detector, a planar mirror and a parabolic mirror or an elliptical mirror or lens for focusing the terahertz wave beam on the detected object.

\* \* \* \* \*